United States Patent

Stenzel et al.

Patent Number: 5,145,849
Date of Patent: Sep. 8, 1992

[54] INDOLYLPROPANOLS AND PREPARATIONS CONTAINING THE COMPOUNDS

[75] Inventors: Wolfgang Stenzel, Reinbek; Ben Armah, Hamburg, both of Fed. Rep. of Germany

[73] Assignee: Beiersdorf Aktiengesellschaft, Hamburg, Fed. Rep. of Germany

[21] Appl. No.: 637,385

[22] Filed: Jan. 3, 1991

[30] Foreign Application Priority Data

Jan. 27, 1990 [DE] Fed. Rep. of Germany ....... 4002391

[51] Int. Cl.$^5$ ..................... A61K 31/44; C07D 401/14; C07D 403/12
[52] U.S. Cl. .................................. 514/210; 546/256; 546/273; 548/467
[58] Field of Search ................ 548/467; 546/273, 256; 514/414, 339, 210

[56] References Cited

U.S. PATENT DOCUMENTS

4,935,414  6/1990  Stenzel et al. ..................... 514/210

FOREIGN PATENT DOCUMENTS

| 0013878 | 8/1980 | European Pat. Off. |
| 0025111 | 3/1981 | European Pat. Off. |
| 0297380 | 1/1989 | European Pat. Off. |
| 2337461 | 2/1975 | Fed. Rep. of Germany |
| 3200304 | 8/1982 | Fed. Rep. of Germany |
| 3524955 | 1/1986 | Fed. Rep. of Germany |
| 3723648 | 1/1989 | Fed. Rep. of Germany |
| 2567885 | 1/1986 | France |
| 2163150 | 2/1986 | United Kingdom |

Primary Examiner—Robert W. Ramsuer
Assistant Examiner—Jacqueline Haley
Attorney, Agent, or Firm—Sprung Horn Kramer & Woods

[57] ABSTRACT

Indolylpropanols of the formula I

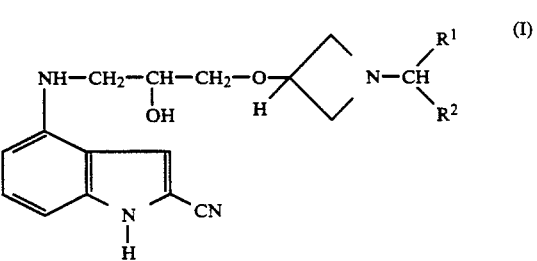

in which $R^1$ and $R^2$, which can be identical or different, in each case denote a 2-, 3- or 4-pyridinyl or a 2- or 3-thienyl radical, phenyl or phenyl which is optionally monosubstituted or identically or differently disubstituted by halogen, alkyl, $C_{3-7}$-cycloalkyl or $C_{1-6}$-alkoxy, where alkyl denotes straight-chain alkyl having 1 to 6 carbon atoms or branched alkyl having 3 to 6 carbon atoms, and their salts and acid addition salts, tautomers and optical isomers show positive inotropic and antiarrhythmic activity.

10 Claims, No Drawings

INDOLYLPROPANOLS AND PREPARATIONS CONTAINING THE COMPOUNDS

DESCRIPTION

The invention relates to novel substituted indolylpropanols of the formula I

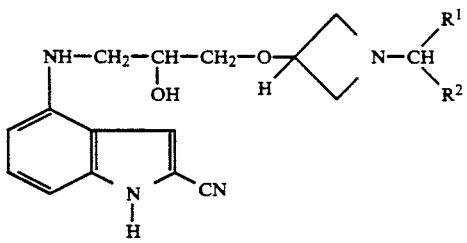

in which $R^1$ and $R^2$, which can be identical or different, in each case denote a 2-, 3- or 4-pyridinyl or a 2- or 3-thienyl radical, phenyl or phenyl which is optionally monosubstituted or identically or differently disubstituted by halogen, alkyl, $C_{3-7}$-cycloalkyl or $C_{1-6}$-alkoxy, where alkyl denotes straight-chain alkyl having 1 to 6 carbon atoms or branched alkyl having 3 to 6 carbon atoms, and their salts and acid addition salts, tautomers and optical isomers, a process for their preparation, their use and preparations which contain these compounds.

For the sake of simplicity, the compounds according to the invention are defined in only one tautomeric form represented by formula I. However, the invention applies to all tautomeric forms of the compounds.

Although pharmaceutically tolerable salts and acid addition salts of the novel compounds of the formula I are preferred, all the salts are within the field of the invention. All the salts are useful for the preparation of the compound, even if the specific salt is only desired as an intermediate, such as, for example, if the salt is only formed for the purposes of purification or identification, or if it is used as an intermediate in the preparation of a pharmaceutically tolerable salt, for example by ion exchange procedures.

The compounds of the general formula I and their salts contain asymmetric carbon atoms. The invention therefore also relates to the various optical isomers and to the diastereoisomers as well as the salts and addition salts of these compounds with acids. The racemates can be resolved into their optical antipodes by methods known per se.

Compounds structurally related to the compounds of the present invention are described in European Patent Applications 25,111 and 297,380 and German Offenlegungsschriften 3,524,955 and 3,723,648. However, the compounds of the present invention are neither specifically disclosed nor suggested by these disclosures.

If not indicated otherwise, the alkyl groups and alkyl moieties of groups according to the invention, for example alkoxy groups, can be straight-chain or branched and in each case preferably have 1 to 6 carbon atoms, preferably 1 to 4 carbon atoms, in particular 1 or 2 carbon atoms. The branched alkyl groups have at least 3 carbon atoms. Preferred alkyls are methyl, ethyl, n-propyl, isopropyl and butyl. Methyl, ethyl, methoxy and ethoxy are particularly preferred.

Cycloalkyl groups according to the invention preferably have 3 to 7 carbon atoms, in particular 3 to 6 carbon atoms. Cyclopropyl and cyclohexyl are particularly preferred.

Pyridinyl is preferably pyridin-4-yl, and thienyl is preferably thien-3-yl. Suitable halogen is fluorine, chlorine, bromine or iodine. Fluorine and chlorine are preferred.

$R^1$ and $R^2$ are preferably unsubstituted phenyl.

The phenyl group can carry one or two of the substituents mentioned, which can be identical or different. If the phenyl groups are disubstituted, the substituents are preferably identical.

Substituted phenyl groups $R^1$ and/or $R^2$ are preferably substituted in the 3- and/or 4-position by the substituents indicated, in particular monosubstituted in the 4-position. Preferred substituents are halogen or alkoxy, in particular halogen.

The following compounds of the formula I, their salts and physiologically tolerable salts are preferred:

a) R,S-4-(3-(1-diphenylmethylazetidin-3-oxy)-2-hydroxypropylamino)-1H-indole-2-carbonitrile
b) R,S-4-(3-(1-(bis-4,4'-fluorophenylmethylazetidin-3-oxy)-2-hydroxypropylamino)-1H-indole-2-carbonitrile
c) R,S,-4-(3-(1-(4-pyridinylphenylmethylazetidin-3-oxy)-2-hydroxypropylamino)-1H-indole-2-carbonitrile The novel compounds of the general formula I in which $R^1$ and $R^2$ have the meaning indicated can be prepared by reaction of the indole derivative II

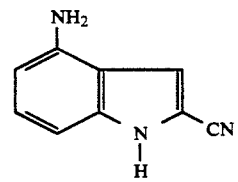

with compounds of the formula III:

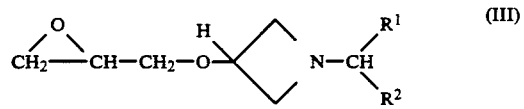

in which $R^1$ and $R^2$ have the abovementioned meaning.

The reactions can be carried out in organic solvents, such as ethanol or dioxane or other suitable solvents in the presence of a base, preferably piperidine, at temperatures between 0° C. and the boiling point of the reaction mixture, preferably at room temperature.

The compounds of the formulae II and III in which $R^1$ and $R^2$ have the abovementioned meaning are known (German Offenlegungsschrift 3,723,648 and European Patent Application 297,380) or can be prepared in analogy to known processes.

The compound a) is particularly preferred.

The compounds of the formula I according to the invention, their physiologically tolerable salts and acid addition salts are therapeutic active compounds, have high pharmacological activity and are useful medicaments. For example, they act as sodium channel modulators. They show, in particular, positive inotropic and antiarrhythmic activity. They are suitable for the treatment of coronary insufficiency and cardiac arrhythmias.

The compounds of the present invention can be used orally or parenterally in humans at a dose of 1–800 mg, preferably 10–200 mg, particularly preferably 20–50 mg per day, in particular in subdivided doses, for example three times daily. These doses are advantageous for the treatment of the abovementioned diseases, in particular of coronary insufficiency and/or arrhythmias.

The positive inotropic activity of the compounds according to the invention was determined on the guinea pig papillary muscle (Naunyn-Schmiedeberg's Arch. Pharmacol. 304,37,1978). The concentration of the substance in the organ bath was $10^{-5}$ mol/1 in each case. The maximum percentage increase in the contraction amplitude was in each case determined on three papillary muscles and was at least 50%.

The invention also relates to the compounds according to the invention for the treatment of the above diseases and to methods, for the treatment of these diseases, in which these compounds are used and to their use as medicaments or their use in methods for the production of agents which contain these compounds for the treatment of these diseases and to processes for the preparation of the compounds.

According to the invention, pharmaceutical compositions are provided which contain a compound of the formula I or its pharmaceutically tolerable salts, if appropriate together with a pharmaceutically tolerable diluent or carrier.

The compounds according to the invention can be mixed with customary pharmaceutically tolerable diluents or carriers and, if appropriate, with other auxiliaries and are administered, for example, orally or parenterally. They can be administered orally in the form of tablets, film tablets, coated tablets, syrups, suspensions and liquids or parenterally in the form of solutions or suspensions. Preparations to be administered orally may contain one or more additives such as sweeteners, flavourings, colorants and preservatives. Tablets may contain the active compound mixed with customary pharmaceutically tolerable auxiliaries, for example inert diluents such as calcium carbonate, sodium carbonate, lactose and talc, granulating agents and agents which promote the disintegration of the tablet on oral administration, such as starch or alginic acid, binders such as starch or gelatine, lubricants such as magnesium stearate, stearic acid and talc.

Suitable excipients are, for example, milk sugar (lactose), gelatine, cornflour, stearic acid, ethanol, propylene glycol, ethers of tetrahydrofurfuryl alcohol and water.

The tablets can be coated by known procedures in order to delay disintegration and absorption in the gastrointestinal tract, as a result of which the activity of the active compound can extend over a longer period of time. In the suspensions, the active compound can also be mixed with auxiliaries which are customary for the preparation of such compositions, for example suspending agents such as methylcellulose, tragacanth or sodium alginate, wetting agents such as lecithin, polyoxyethylene stearate and polyoxyethylene sorbitan mono-oleate and preservatives such as ethyl parahydroxybenzoate. Capsules can contain the active compound as an individual component or mixed with a solid diluent such as calcium carbonate, calcium phosphate or kaolin. The injectable preparations are also formulated in a manner known per se. The pharmaceutical preparations can contain the active compound in an amount of 0.1 to 90%, in particular 1 to 90%, the remainder being an excipient or additive. With respect to preparation and administration, solid preparations such as tablets and capsules are preferred. The preparations preferably contain the active compound in an amount of 1–30 mg.

The compounds of the general formula I can be either bases or acids or amphoteric and are therefore isolated from the reaction mixtures in the form of their salts or acid addition salts. As bases, they can be converted into salts with suitable inorganic or organic acids by known methods or, as acids, can form salts with bases.

Physiologically tolerable salts or acid addition salts are preferred. For this purpose, suitable inorganic acids are, for example, sulphuric acid or hydrohalic acids, for example hydrochloric acid, and suitable organic acids are, for example, fumaric acid, maleic acid, citric acid and tartaric acid. To prepare these salts, an alcoholic solution of a suitable acid is added to a hot alcoholic solution of the base and the salt is obtained after addition of ether. Preferred salts are the alkali metal, alkaline earth metal and ammonium salts of the compounds of the formula I which are obtained with the corresponding bases, in particular sodium hydroxide or potassium hydroxide.

The compounds of the formula I according to the invention have a centre of chirality on carbon atom 2 of the propoxy side-chain and, depending on the substituents, can have other asymmetric carbon atoms and therefore exist as racemates and diastereoisomers. Diastereoisomers can be separated into their racemic modifications in a known manner by virtue of the physico-chemical differences between their constituents. Racemates can be separated by known methods, for example by recrystallising in optically active solvents, by means of microorganisms or reaction with an optically active acid or base which forms a salt with the racemic compound, separation of the diastereoisomers by fractional crystallisation and liberation of the enantiomers by suitable agents. Particularly suitable optically active acids are, for example, the d- and l-forms of tartaric acid, ditoluyltartaric acid, malic acid, mandelic acid, camphorsulphonic acid or pyrrolidonecarboxylic acid. Suitable optically active bases are alpha-phenylethylamine, methylamine, ephedrine, brucine and quinine. The more active of the antipodes is advantageously isolated. However, according to the invention it is also possible to obtain the pure enantiomers by asymmetric synthesis.

The invention also relates to a process for the production of pharmaceutical preparations, characterised in that a compound of the formula I and/or of one of its physiologically acceptable salts is brought into a suitable dose form together with at least one solid, liquid or semi-liquid excipient or auxiliary and, if appropriate, in combination with one or more other active compounds.

The following examples are used to illustrate the invention.

EXAMPLE 1

(R,S)-4-(3-(1-diphenylmethylazetidin-3-oxy)-2-hydroxypropylamino)-1H-indole-2-carbonitrile 7.5 g of aminoindole-2-carbonitrile and 16.1 g of 1-(diphenylmethyl)-3-(2,3-epoxypropoxy)azetidine are heated under reflux in 120 ml of ethanol in the presence of a few drops of piperidine for 24 hours and the mixture is then concentrated to dryness in vacuo. The crude reaction mixture is stirred in diethyl ether, the insoluble residue is filtered off and the ether phase is concentrated. The compound prepurified in this way is purified by column chromatography on silica gel. (CH₂Cl₂/ethanol 99:1)

Yield: 4.2 g (18%)

m.p.: 88°–89° C.

EXAMPLE 2

Production of Ampoules

Ampoules which contain the constituents mentioned in the following can be prepared in a known manner. The active compound is dissolved in water and 1,2-propanediol and the solution is poured into glass ampoules under nitrogen.

(R,S)-4-(3-(1-diphenylmethylazetidin-3-oxy)-2-hydroxypropylamino)-1H-indole-2-carbonitrile 1 mg
1,2 propanediol 0.8 ml distilled water to 2.0 ml

EXAMPLE 3

Production of Tablets and Capsules

Tablets and capsules which contain the constituents indicated below are prepared by known procedures. These tablets and capsules are suitable for the treatment of the abovementioned diseases, in particular coronary insufficiency, in dosages of in each case one tablet or capsule three times daily.

| Constituents | Weight (mg) Tablet | Capsule |
|---|---|---|
| (R,S)-4-(3-(1-diphenyl-methylazetidin-3-oxy)-2-hydroxypropylamino)-1H-indole-2-carbonitrile | 10 | 5 |
| Tragacanth | 10 | |
| Lactose | 247.5 | 300 |
| Cornflour | 25 | |
| Talc | 15 | |
| Magnesium stearate | 2.5 | |

The compounds of the formula I' according to the invention

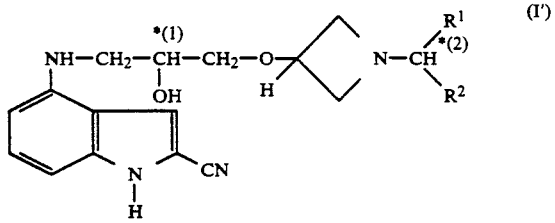

indicated in the following table can be obtained analogously to the above examples. (Examples 4–13): "rac" denotes racemic.

"—" denotes that no asymmetric carbon atom is present.

| Example | R¹ | R² | Config. C* (1) | Config. C* (2) |
|---|---|---|---|---|
| 4 | 4-F-phenyl | 4-F-phenyl | rac | — |
| 5 | 4-OCH₃-phenyl | 4-OCH₃-phenyl | rac | — |
| 6 | 4-CH₃-phenyl | 4-CH₃-phenyl | rac | — |
| 7 | 4-Cl-phenyl | phenyl | rac | rac |
| 8 | 4-pyridinyl | phenyl | rac | rac |
| 9 | 3-pyridinyl | phenyl | rac | rac |
| 10 | 4-pyridinyl | 4-pyridinyl | rac | — |
| 11 | 2-thienyl | phenyl | rac | rac |
| 12 | 3-thienyl | phenyl | rac | rac |
| 13 | 2-thienyl | 2-thienyl | rac | — |

EXAMPLE 14

1-(Diphenylmethyl-3-(2,3-epoxypropoxy)azetidine 37.5 g of diphenylmethylazetidin-3-ol are dissolved in a mixture of 250 ml of dimethyl sulphoxide and 150 ml of 5% strength sodium hydroxide solution at room temperature, 65 ml of epichlorohydrin are added and the reaction mixture is allowed to stand at room temperature for 3 days. It is then extracted using 300 ml of methylene chloride, and the organic phase is dried over sodium sulphate and concentrated. The crude product is distilled in vacuo.

Yield: 29.0 g 1-(Diphenylmethyl)-3-(2,3-epoxypropoxy)azetidine b.p. 174°–176° C., 0.2 mbar

We claim:

1. A substituted indolylpropanol of the formula

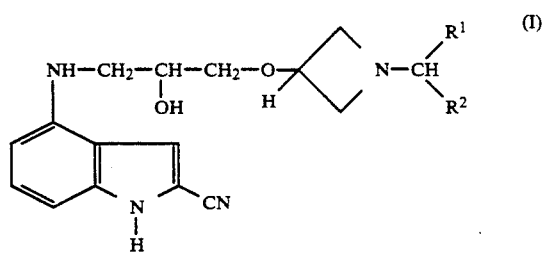

in which

R¹ and R² each independently is a 2-, 3- or 4-pyridinyl radical, a 2- or 3-thienyl radical, phenyl or phenyl mono- or di-substituted by a radical independently selected from the group consisting of halogen, $C_{1-6}$-alkyl, $C_{3-7}$-cycloalkyl and $C_{1-6}$-alkoxy, or a salt, acid addition salt, tautomer or optical isomer thereof.

2. A compound according to claim 1, in racemic or enantiomeric form.

3. A compound according to claim 1, wherein such compounds is (R,S)-4-(3-(1-diphenylmethylazetidine-3-oxy)-2-hydroxypropylamino)-1H-indole-2-carbonitrile or a salt, acid addition salt, tautomer or optical isomer thereof.

4. A compound according to claim 1, wherein such compound is R,S-4-(3-(1-(bis-4,4'-fluorophenylmethyl)azetidin-3-oxy)-2-hydroxypropylamino)-1H-indole-2-carbonitrile or a salt, acid addition salt, tautomer or optical isomer thereof.

5. A compound according to claim 1, wherein such compound is R,S-4-(3-(1-(4-pyridinylphenylmethyl)-azetidin-3-oxy)-2-hydroxypropylamino)-1H-indole-2-carbonitrile or a salt, acid addition salt, tautomer or optical isomer thereof.

6. A sodium channel modulating composition comprising an amount effective therefor of a compound according to claim 1 or a salt, acid addition salt, tautomer or optical isomer thereof, and a pharmaceutically acceptable diluent.

7. A method of modulating the sodium channel in a patient in need thereof which comprises administering to such patient an amount effective therefor of a compound according to claim 1 or a salt, acid addition salt, tautomer or optical isomer thereof.

8. A method of modulating the sodium channel in a patient in need thereof which comprises administering to such patient an amount effective therefor of a compound according to claim 3 or a salt, acid addition salt, tautomer or optical isomer thereof.

9. A method of modulating the sodium channel in a patient in need thereof which comprises administering to such patient an amount effective therefor of a compound according to claim 4 or a salt, acid addition salt, tautomer or optical isomer thereof.

10. A method of modulating the sodium channel in a patient in need thereof which comprises administering to such patient an amount effective therefor of a compound according to claim 5 or a salt, acid addition salt, tautomer or optical isomer thereof.

* * * * *